(12) United States Patent
Loesel et al.

(10) Patent No.: US 10,716,706 B2
(45) Date of Patent: Jul. 21, 2020

(54) SYSTEM AND METHOD FOR PERFORMING LENS FRAGMENTATION

(75) Inventors: Frieder Loesel, Mannheim (DE);
Jochen Kandulla, Munich (DE);
Friedrich Moritz, Munich (DE);
Gwillem Mosedale, Munich (DE);
Holger Schlueter, Munich (DE);
Roland Toennies, Gernlinden (DE);
Gerhard Youssefi, Landshut (DE);
David Haydn Mordaunt, Los Gatos, CA (US)

(73) Assignees: BAUSCH & LOMB INCORPORATED, Rochester, NY (US); TECHNOLAS PERFECT VISION GMBH, Munich (DE)

(*) Notice: Subject to any disclaimer, the term of this patent is extended or adjusted under 35 U.S.C. 154(b) by 1740 days.

(21) Appl. No.: 13/436,352

(22) Filed: Mar. 30, 2012

(65) Prior Publication Data

US 2012/0259320 A1 Oct. 11, 2012

Related U.S. Application Data

(60) Provisional application No. 61/473,044, filed on Apr. 7, 2011.

(51) Int. Cl.
*A61F 9/008* (2006.01)

(52) U.S. Cl.
CPC .. *A61F 9/00825* (2013.01); *A61F 2009/0087* (2013.01); *A61F 2009/00851* (2013.01); *A61F 2009/00887* (2013.01)

(58) Field of Classification Search
CPC ... A61F 9/00–9/013; A61F 9/008–2009/00897
(Continued)

(56) References Cited

U.S. PATENT DOCUMENTS 3,589,363 A 6/1971 Banko et al.
3,805,787 A 4/1974 Banko
(Continued)

FOREIGN PATENT DOCUMENTS

WO 2006074469 A2 7/2006
WO 2007084694 A2 7/2007
(Continued)

OTHER PUBLICATIONS

Dodick, Jack M., and Iman Ali Pahlavi. "Lasers in small-incision cataract surgery." Lasers in ophthalmology: basic diagnostic and surgical aspects. Amsterdam, the Netherlands: Kugler Publications (2003): 395-402. ISBN 9789062991891.*
(Continued)

*Primary Examiner* — Gary Jackson
*Assistant Examiner* — Jonathan T Kuo
(74) *Attorney, Agent, or Firm* — Michael L. Smith

(57) ABSTRACT

A system and method are provided for fragmenting a crystalline lens, to facilitate its removal from the lens bag during an ophthalmic laser surgery. First, a predetermined pattern is used to make Laser Induced Optical Breakdown (LIOB) cuts that section the lens into asymmetrical, operational segments. At least one operational segment is then selected and softened with a plurality of compact LIOB cuts. Once softened, the selected segment is aspirated. The remaining operational segments are then subsequently removed. During a procedure, an imaging unit can monitor movements of the lens bag to ensure proper placement of the LIOB cuts on the lens.

10 Claims, 4 Drawing Sheets

(58) Field of Classification Search
USPC .............................................. 606/4–6, 10–12
See application file for complete search history.

(56) References Cited

U.S. PATENT DOCUMENTS

| | | | |
|---|---|---|---|
| 3,941,122 A | 3/1976 | Jones | |
| 4,428,748 A | 1/1984 | Peyman et al. | |
| 4,531,934 A | 7/1985 | Kossovsky et al. | |
| 4,538,608 A | 9/1985 | L'Esperance, Jr. | |
| 4,634,420 A | 1/1987 | Spinosa et al. | |
| 5,246,435 A | 9/1993 | Bille et al. | |
| 5,403,307 A | 4/1995 | Zelman | |
| 5,439,462 A | 8/1995 | Bille et al. | |
| 5,702,441 A | 12/1997 | Zhou | |
| 5,733,276 A | 3/1998 | Belkin | |
| 5,865,831 A | 2/1999 | Cozean et al. | |
| 6,059,772 A | 5/2000 | Hsia et al. | |
| 6,467,906 B1 | 10/2002 | Alpins | |
| 6,506,176 B1* | 1/2003 | Mittelstein | A61F 9/013 604/107 |
| 6,514,241 B1 | 2/2003 | Hsia et al. | |
| RE40,420 E | 7/2008 | Dick et al. | |
| 7,621,637 B2 | 11/2009 | Rathjen et al. | |
| 2005/0165387 A1 | 7/2005 | Lubatschowski et al. | |
| 2006/0195076 A1 | 8/2006 | Blumenkranz et al. | |
| 2006/0200113 A1 | 9/2006 | Haffner et al. | |
| 2007/0173785 A1 | 7/2007 | Frey et al. | |
| 2007/0173794 A1 | 7/2007 | Frey et al. | |
| 2007/0185475 A1 | 8/2007 | Frey et al. | |
| 2008/0281301 A1* | 11/2008 | DeBoer | A61B 34/10 606/1 |
| 2008/0281303 A1 | 11/2008 | Culbertson et al. | |
| 2009/0012507 A1* | 1/2009 | Culbertson | A61F 2/16 606/6 |
| 2009/0125005 A1 | 5/2009 | Chemyak et al. | |
| 2009/0137991 A1 | 5/2009 | Kurtz | |
| 2009/0137993 A1 | 5/2009 | Kurtz | |
| 2009/0149840 A1 | 6/2009 | Kurtz | |
| 2009/0149841 A1 | 6/2009 | Kurtz | |
| 2009/0171327 A1* | 7/2009 | Kurtz | A61F 9/008 606/6 |
| 2009/0177189 A1 | 7/2009 | Raksi | |
| 2010/0004641 A1 | 1/2010 | Frey et al. | |
| 2010/0022995 A1 | 1/2010 | Frey et al. | |
| 2010/0022996 A1 | 1/2010 | Frey et al. | |
| 2010/0042079 A1 | 2/2010 | Frey et al. | |
| 2010/0076417 A1* | 3/2010 | Suckewer | A61F 9/00838 606/4 |
| 2010/0137850 A1 | 6/2010 | Culbertson et al. | |
| 2010/0292678 A1* | 11/2010 | Frey | A61F 9/008 606/5 |
| 2010/0324542 A1 | 12/2010 | Kurtz | |
| 2010/0324543 A1 | 12/2010 | Kurtz et al. | |
| 2011/0022036 A1 | 1/2011 | Frey et al. | |
| 2011/0040293 A1 | 2/2011 | Bor | |
| 2011/0166557 A1 | 7/2011 | Naranjo-Tackman et al. | |
| 2011/0184392 A1 | 7/2011 | Culbertson et al. | |
| 2011/0184395 A1 | 7/2011 | Schuele et al. | |
| 2011/0196350 A1* | 8/2011 | Friedman | A61F 9/008 606/6 |
| 2011/0202044 A1 | 8/2011 | Goldshleger et al. | |
| 2011/0202046 A1 | 8/2011 | Angeley et al. | |
| 2012/0172854 A1 | 7/2012 | Raymond et al. | |
| 2014/0194859 A1* | 7/2014 | Ianchulev | A61F 9/00736 606/6 |
| 2014/0364870 A1* | 12/2014 | Alvarez | A61B 19/2203 606/130 |

FOREIGN PATENT DOCUMENTS

| | | |
|---|---|---|
| WO | 2009089504 A2 | 7/2009 |
| WO | 2009090095 A1 | 7/2009 |

OTHER PUBLICATIONS

PCT International Search Report, Application No. PCT/IB2012/000703, dated Apr. 5, 2012.

* cited by examiner

SYSTEM AND METHOD FOR PERFORMING LENS FRAGMENTATION

This application claims the benefit of U.S. Provisional Patent Application Ser. No. 61/473,044, filed Apr. 7, 2011.

FIELD OF THE INVENTION

The present invention pertains to ophthalmic surgery. More particularly, the present invention pertains to systems and methods for removing the lens from its lens bag during an ophthalmic surgical procedure. The present invention is particularly, but not exclusively, useful as a system and method for facilitating the removal of the lens by performing Laser Induced Optical Breakdown (LIOB) on the lens to fragment the lens prior to its removal from the lens bag.

BACKGROUND OF THE INVENTION

In a typical lens removal procedure (i.e. a capsulotomy), the anterior portion of the lens bag that holds the crystalline lens of an eye is perforated to create a rhexis. The lens is then removed through the rhexis. In place of the removed lens, a prosthetic Intraocular Lens (IOL) is inserted into the lens bag. Two of the primary objectives of a lens removal procedure are that the implanted prosthetic IOL will function in the stead of the removed lens and that damage to the lens bag and other tissue in the eye will be substantially avoided, or at least minimized.

Heretofore, one method commonly used for removing the lens from its lens bag has involved phacoemulsification of the lens. In such a procedure, ultrasound waves break down lens tissue, and after the tissue has been sufficiently broken down it is aspirated. The intraocular lens (IOL) is then inserted into the lens bag.

Apart from phacoemulsification, it is also well known that lasers are very useful for altering lens tissue in the eye of a patient. More specifically, it is known that lens tissue can be effectively altered (i.e. photoablated) by a phenomenon that is widely referred to as Laser Induced Optical Breakdown (LIOB). An important result of LIOB is that very fine cuts through the tissue can be accomplished quickly. Moreover, these LIOB cuts can be made with great precision. A consequence of the ability of an LIOB procedure to cut into tissue is that due to the fineness of the cuts, and due to the ability to precisely control their placement, LIOB cuts can be made in compact patterns that will effectively pulverize lens tissue.

When performing a capsulotomy, it is clearly advantageous to accomplish the procedure as quickly as possible. This requirement then leads to a need for minimizing the time that is necessary to prepare the lens for removal. Actual removal of the lens tissue from the bag will then be dependent on the size and location of the rhexis that is used for the procedure.

In light of the above, it is an object of the present invention to provide a system and method for performing lens fragmentation with Laser Induced Optical Breakdown (LIOB) techniques that can be accomplished quickly, with great precision. Another object of the present invention is to effectively minimize the size of a rhexis that is required for the removal of a crystalline lens from its bag. Yet another object of the present invention is to provide a system and method for performing lens fragmentation which is simple to use, is easy to implement, and is relatively cost effective.

SUMMARY OF THE INVENTION

In accordance with the present invention, a system and method for preparing the lens of an eye for removal from its lens bag during ophthalmic (cataract) surgery requires a computer controlled laser unit. Functionally, this unit performs Laser Induced Optical Breakdown (LIOB) in two different patterns of cuts that extend through the lens tissue of the eye. These patterns are a predetermined pattern that extends over the entire lens, and a defined pattern that is confined to a selected segment of the lens.

Preparation of the lens is accomplished by first sectioning the lens tissue into operational segments. This is done by cutting the lens with a plurality of LIOB cuts that are arranged in the predetermined pattern. Typically, the predetermined pattern will be made up of radial cuts, ring cuts or a combination thereof that collectively section the lens into the desired operational segments. The present invention also envisions that the sectioning of the lens with the predetermined pattern can be accomplished by a partial dissection of tissue, such as by perforating the tissue. Importantly, in any case, the predetermined pattern of LIOB cuts does not effectively weaken the lens tissue.

For the present invention, at least one, but possibly more, of the operational segments is (are) designated as a selected segment. This selected segment includes a targeted surface at which the laser unit is directed. Compact LIOB cuts are then made in the defined pattern within at least a portion of lens tissue in the selected segment. The objective of using this defined pattern of compact cuts is to soften (i.e. pulverize) lens tissue in the selected segment. Preferably, the selected segment will include somewhere between approximately 5% and 40% of the total lens tissue, by volume. Further, as a practical matter, the selected segment is typically a quadrant of the lens that extends generally from a defined axis of the eye to the periphery of the lens, and includes tissue between the anterior and the posterior surfaces of the lens. Thus, relative to the defined axis, the selected segment is asymmetrical. In any event, the consequence of the predetermined pattern and the subsequent defined pattern of cuts is that the lens is prepared to be more easily accessed and manipulated inside the lens bag for removal of the lens from the lens bag.

Structurally, the system of the present invention includes the above-mentioned laser unit for generating a pulsed laser beam. And, it includes a computer that is electronically connected to the laser unit. Within this structure, a computer program is used for guiding the focal point of the laser beam. Further, the system also preferably includes an aspirator and an irrigator that work together for removing lens tissue from the lens bag, and may be included as parts of the same device. In addition, the lens tissue can be removed from the lens bag with the help of low power phacoemulsification as required. Additionally, an important aspect of the present invention is the use of a probe, or some similar means, for moving the lens in the lens bag during aspiration of the lens. Specifically, this manipulation facilitates the aspiration of lens tissue from the lens bag. As envisioned for the system of the present invention, after the lens has been prepared with the predetermined and defined patterns of LIOB cuts, the actual removal of lens tissue from the lens bag can be accomplished either manually by the surgeon or by using robotics. When the system uses robotics, the surgeon inputs commands into a robotic interface device connected to the computer. These commands are then used to control the aspirator, the irrigator, and the probe.

In addition to the above, the system may also include an imaging unit for creating an image of the eye. When an imaging unit is used, the resultant image is sent to the computer where it is used for selecting appropriate predetermined and defined patterns for the LIOB cuts. In each case, subject to an override function by the operator, the selections of the predetermined and defined patterns can be accomplished by the computer. Furthermore, these selections are made according to parameters such as: 1) optical characteristics of the lens; 2) the size of the lens; and 3) the shape of the lens. Typically, relative to an axis defined by the lens (e.g. the visual axis or another axis of the eye), the predetermined pattern of LIOB cuts will preferably be either a plurality of radial cuts extending outwardly from the axis, a plurality of ring cuts substantially centered on the axis, or a combination of the two. On the other hand, the defined pattern of compact LIOB cuts will typically be a selection of line cuts, cube cuts, statistically arbitrary cuts, sphere-like cuts, wave cuts, polygonal cuts, radial cuts, arc cuts, combinations of these or any cut that can be described by an expansion series.

A further purpose for the imaging unit is to detect movement of the lens in the lens bag during the procedure. This is accomplished by using the imaging unit to produce an initial image of the lens bag prior to any type of LIOB cuts being performed. Subsequently, upon the initiation of compact LIOB cuts, an actual image is produced in real-time by the imaging device. The initial image and the actual image are then compared to each other by the computer. Any difference between the initial image and the actual image is indicative of an unwanted movement of the lens in the lens bag. When a difference is detected, the computer will then realign the laser unit to minimize or compensate for the difference. Thus, the system ensures that the focal point of the laser beam follows the path required to produce the predetermined path and the defined path.

In operation, a method for preparing the lens of an eye for removal from its lens bag requires sectioning the lens with a predetermined pattern of Laser Induced Optical Breakdown (LIOB) cuts. As mentioned above, this sections the lens into a plurality of operational segments. Next, compact LIOB cuts are made in a defined pattern on tissue in a selected segment of the lens. Furthermore, it is envisioned that the defined pattern may not necessarily cover the entire selected segment. As mentioned above, during the creation of the compact LIOB cuts, the computer is constantly monitoring the position of the lens bag to confirm that no displacement of the lens bag has occurred.

Once lens tissue in the selected segment has been softened, it can then be easily accessed and aspirated to remove the softened lens tissue from the lens bag. Importantly, this aspiration (i.e. removal) can be accomplished while the lens bag is irrigated. As envisioned for the present invention, further aspiration is done in a particular sequence. First, at least a portion of the softened lens tissue in the selected segment is removed from the lens bag. Next, un-softened tissue from outside the selected segment (i.e. remaining operational segments) is removed. Further, as tissue is aspirated from the selected segment, a probe can be inserted into the lens bag and used to turn the lens inside the lens bag to facilitate tissue removal from the bag. Specifically, this is done to reposition the lens for ease in aspirating lens tissue from the lens bag.

It will be appreciated by the skilled artisan that, in addition to ophthalmic applications, the methodologies disclosed for the present invention are also applicable to procedures involving a wide variety of different transparent materials. In these applications, it is envisioned that a computer-controlled laser unit will be employed. In general, the present invention envisions the use of a computer program product that will control the laser beam during the preparation of a transparent material for removal from a bag. Such a computer program product will typically include program sections for: using the laser beam to create an opening in the bag; sectioning the transparent material, in situ, into a plurality of operational segments, with Laser Induced Optical Breakdown (LIOB) cuts into the transparent material; selecting at least one asymmetrically oriented operational segment of the transparent material; creating compact LIOB cuts into the selected segment to soften transparent material in the selected segment; removing the softened selected segment from the bag; and subsequently removing any remaining operational segments from the bag.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
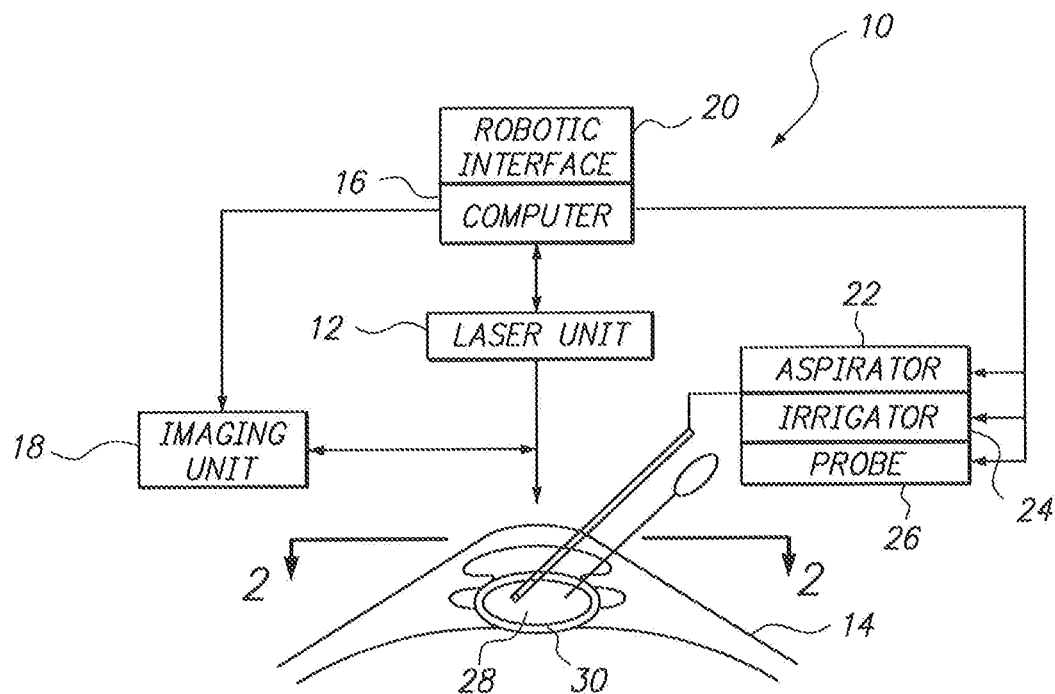
FIG. 1 is a schematic diagram of components for the system of the present invention shown in an operational environment.

Referring initially to FIG. 1, a system for performing lens fragmentation during ophthalmic laser surgery is shown and is generally designated 10. As shown, the system 10 includes a laser unit 12 for performing Laser Induced Optical Breakdown (LIOB) on an eye 14 of a patient (not shown). Further, system 10 also includes a computer 16 for controlling the laser unit 12, and it includes an imaging unit 18 for producing an image of the eye 14 for use in planning and performing the lens fragmentation procedure.

FIG. 1 also indicates that the computer 16 includes a robotic interface device 20 that is selectively employed to allow the system 10 to be operated robotically. In detail, the robotic interface device 20 provides input commands for the computer 16 to collectively control: an aspirator 22, an irrigator 24, and a probe 26. As shown in FIG. 1, these three components are used to manipulate a lens 28 of the eye 14 during the lens fragmentation procedure.

Figures 2A, 2B:
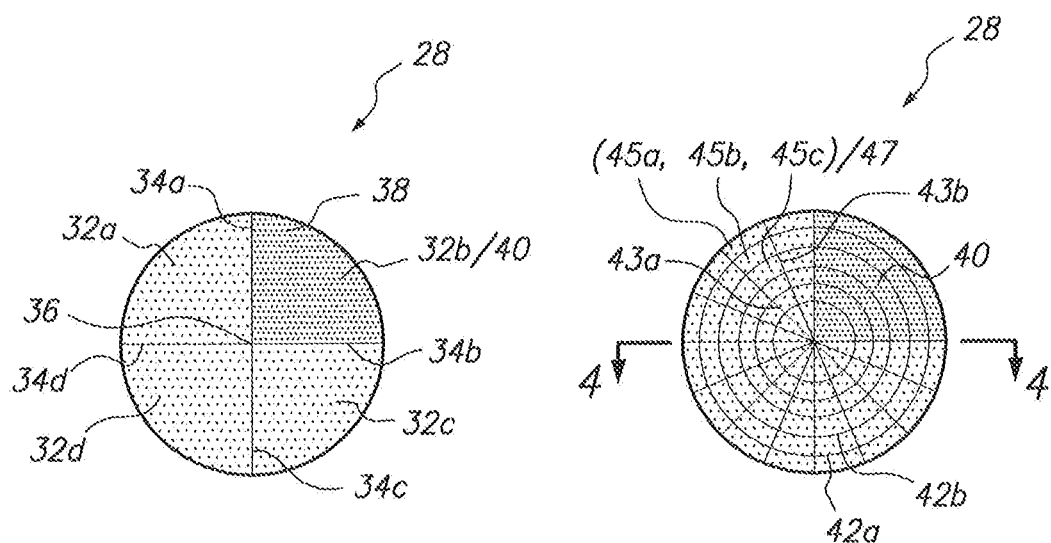
FIG. 2A is a top view of the lens of an eye as seen along the line 2-2 in FIG. 1.
FIG. 2B is a view of the lens as seen in FIG. 2A with a composite of predetermined patterns.

Referring now to FIG. 2A, a top view of the lens 28 of the eye 14 is shown as it has been sectioned into a plurality of operational segments 32a-d. In this exemplary illustration, each operational segment 32a-d is essentially a quadrant of the lens 28. Other configurations for the operational segments 32*a-d* can, however, also be used to accomplish the purposes of the present invention. To section the lens 28 in the manner shown in FIG. 2A, the laser unit 12 makes a plurality of LIOB cuts through the lens 28 in a predetermined pattern. In this case, illustrated in FIG. 2A, the predetermined pattern has been created using a plurality of radial cuts 34*a-d* that each extends from an axis 36 to the outer periphery 38 of the lens 28. In FIG. 2A, for purposes of disclosure only, the operational segment 32*b* is shown shaded in order to identify it as a selected segment 40. As a selected segment 40, it will eventually be cut by a plurality of compact LIOB cuts 41*a-f* (see FIGS. 3A-3F). Moreover, as shown, the selected segment 40 is preferably offset, and is therefore an asymmetric portion of the lens 28.

FIG. 2B illustrates alternative methods for sectioning the lens 28. For example, a predetermined pattern can be used by the laser unit 12 to create both a plurality of ring cuts 42, of which cuts 42*a-b* are exemplary, and a plurality of radial cuts 43, of which cuts 43*a-b* are exemplary. In the event, the ring cuts 42, together with the radial cuts 43, create a plurality of contiguous operational segments 45 (of which the operational segments 45*a-c* shown in FIG. 2B are exemplary). The operational segments 45*a-c* are then chosen to collectively form a selected segment 47.

Figure 3A:
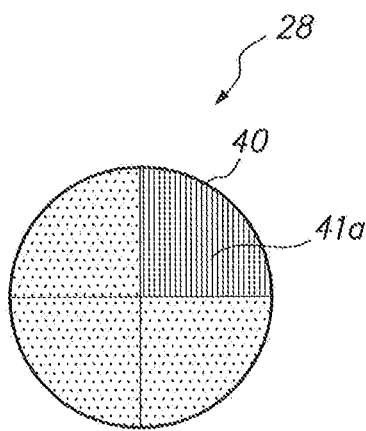
FIGS. 3A-F are views of the lens as shown in FIG. 2A, with different defined patterns of LIOB cuts shown in a selected segment of the lens. Respectively, these defined patterns are: line cuts (FIG. 3A), cube cuts (FIG. 3B), sphere-like cuts (FIG. 3C), statistically arbitrary cuts (FIG. 3D), wave cuts (FIG. 3E), and polygonal cuts (FIG. 3F)
Figure 3B:
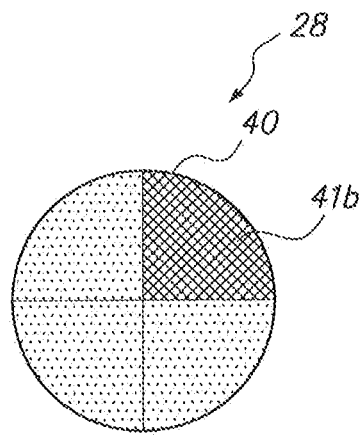
Figure 3C:
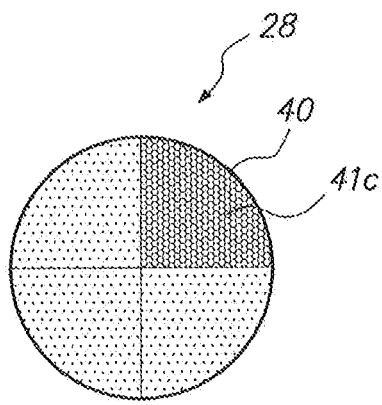
Figure 3D:
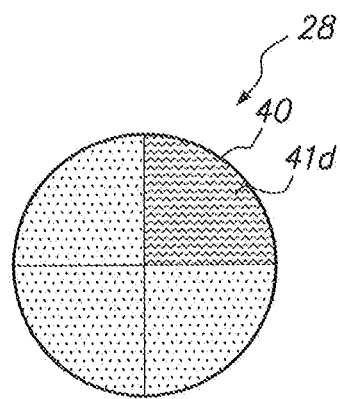
Figure 3E:
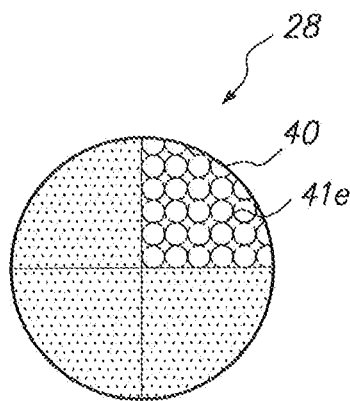
Figure 3F:
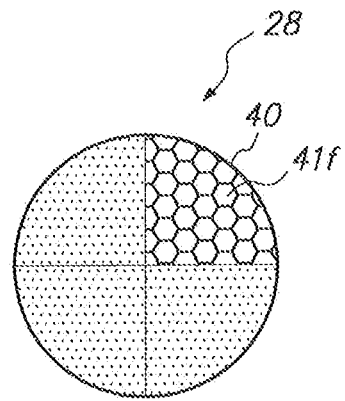
Figure 4:
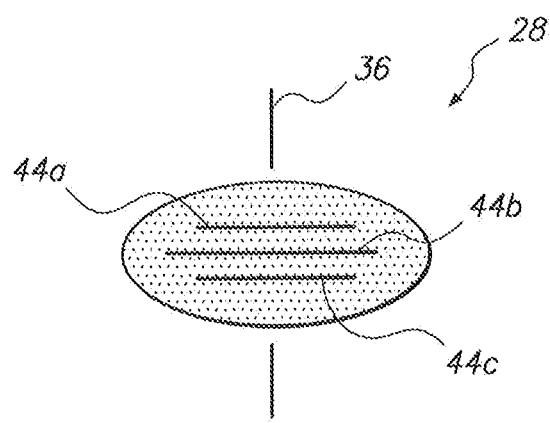
FIG. 4 is a cross sectional view of the lens as seen along the line 4-4 in FIG. 2B showing disk layer cuts oriented perpendicular to an axis defined by the lens.

Referring collectively to FIGS. 3A-3F, six views of the lens 28 of FIG. 2A are shown with each having a different defined pattern of compact LIOB cuts 41 in the selected segment 40 of the lens 28. By way of example, these views show the following types of compact LIOB cuts 41*a-f*, respectively: line cuts (FIG. 3A), cube cuts (FIG. 3B), sphere-like cuts (FIG. 3C), statistically arbitrary cuts (FIG. 3D), wave cuts (FIG. 3E), and polygonal cuts (FIG. 3F). It will also be appreciated that a combination of any of the cuts in the defined patterns shown in FIGS. 3A-3F can also be used to establish the defined pattern for the system 10. Further, as shown in FIG. 4, a plurality of disk, layer cuts 44*a-c* can be oriented perpendicular to the axis 36 inside the lens 28 to help soften tissue in the lens 28. These disk layer cuts 44*a-c* can be made in place of, or in conjunction with, a selected compact LIOB cut 41 to create the defined pattern as disclosed above.

Figure 5A:
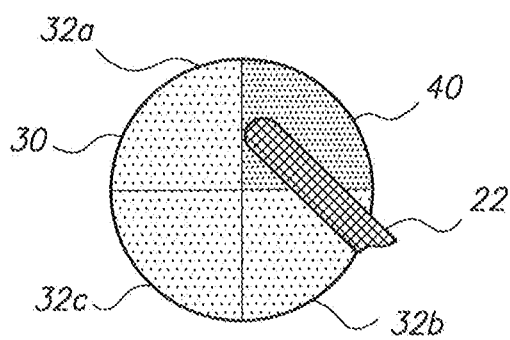
FIGS. 5A-D show a sequence of operational steps for aspirating softened lens tissue from a lens bag in accordance with the present invention.
Figure 5B:
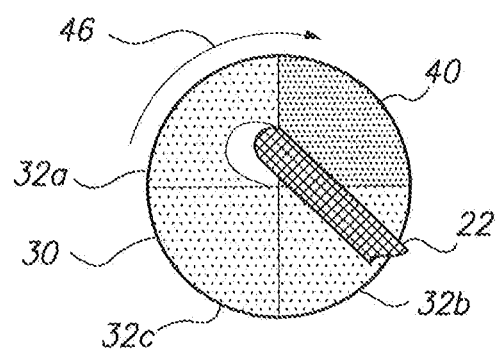
Figure 5C:
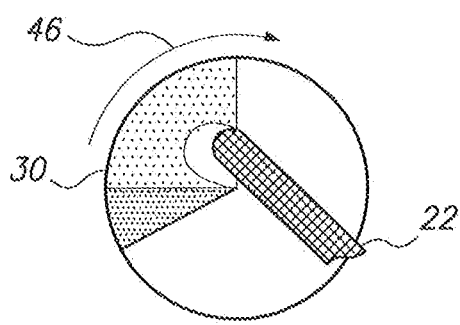
Figure 5D:
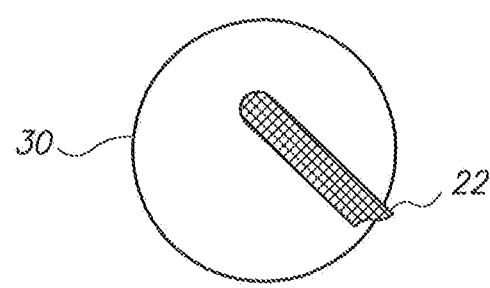

With reference to FIGS. 5A-5D, a sequence of operational steps for aspirating softened lens tissue from the lens bag 30 in accordance with the present invention is shown. To begin the aspiration of the lens 28, and as shown in FIG. 5A, the aspirator 22 is inserted into the lens bag 30. It should be noted that the aspirator 22 can serve a dual-purpose and can be configured to act as both the aspirator 22 and the irrigator 24 for the system 10 when required. It can be seen that the aspirator 22 in FIG. 5A is initially used to aspirate softened tissue from the selected segment 40 of the lens 28. After the selected segment 40 has been effectively aspirated, tissue of the remaining operational segments 32*a*, 32*c* and 32*d* are then aspirated. During a procedure, the probe 26 is used to rotate the lens 28 in the direction of arrow 46 as shown in FIGS. 5B and 5C. The purpose of rotating the lens 28 is two-fold. For one, additional tissue is moved closer to the aspirator 22 to facilitate aspiration. For another, moving the lens 28 allows the aspirator 22 to remain stationary, which lessens the chance of the aspirator 22 damaging the lens bag 30 or other tissue in the eye 14. This process of aspirating and rotating occurs as shown in FIG. 5C until the lens 28 is completely removed from the lens bag 30 (see FIG. 5D). Throughout the aspiration process detailed here, the lens bag 30 may also be irrigated as required. Also, hydrodissection may or may not be performed prior to turning.

Figure 6:
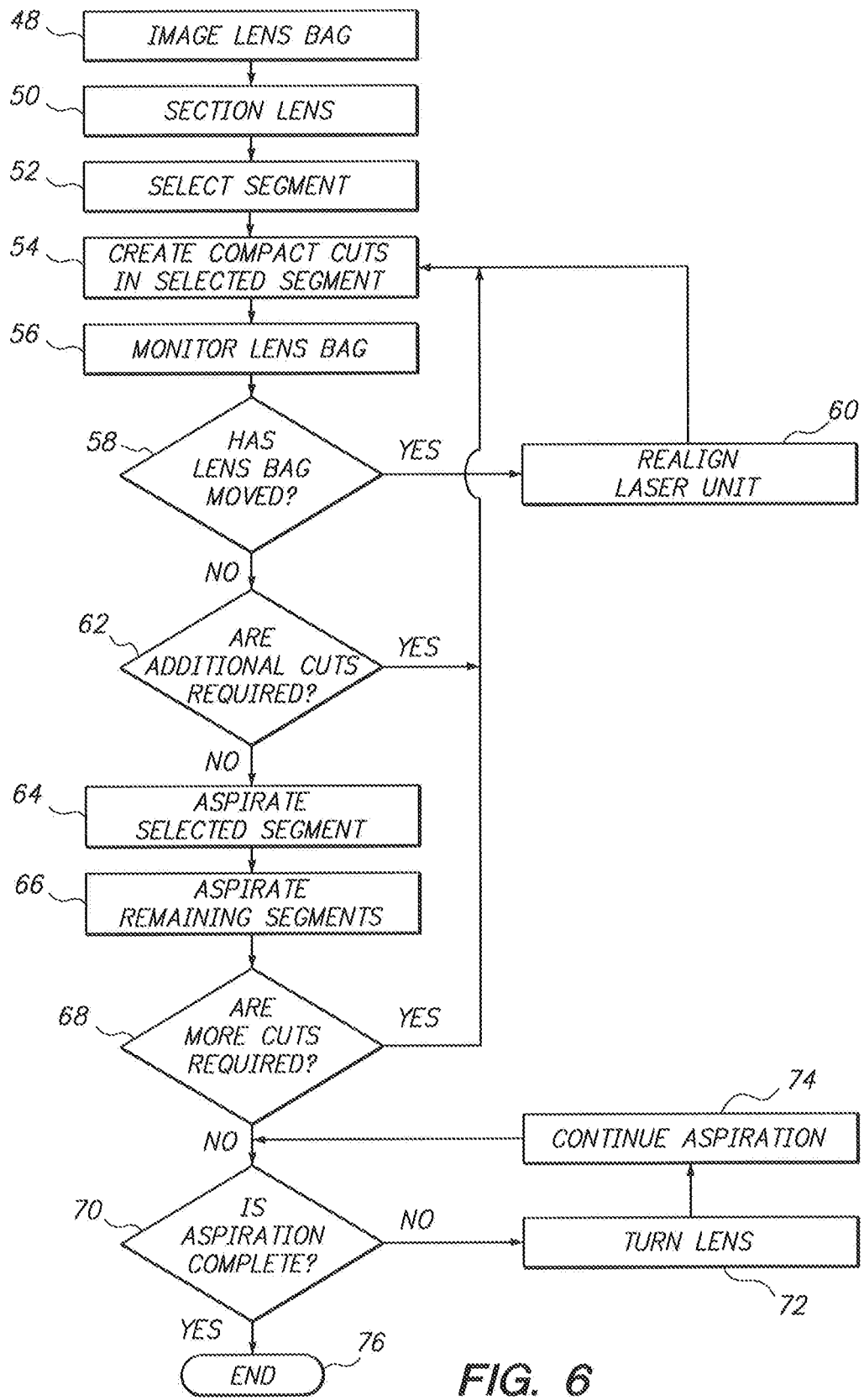
FIG. 6 is a flow chart of an operation of the present invention.

An operation of the present invention can be described using the flow chart shown in FIG. 6. To commence an operation, the imaging unit 18 creates an initial image of the lens bag 30 as shown in action block 48. This image can serve several purposes. For one, the image can be used to establish the initial position of the lens bag 30. For another, it can serve to orient the predetermined pattern for sectioning the lens 28. Also, it can be used to identify the selected segment 40 of the lens 28. After this initial image is created, the lens 28 is sectioned into operational segments 32 at action block 50, and a segment is selected to be targeted for compact LIOB cuts as indicated by action block 52. Next, the laser unit 12 creates the compact LIOB cuts in the selected segment 40 of the lens 28 as shown in action block 54.

An important consideration when directing the laser unit 12 to the selected segment 40 is ensuring that the lens bag 30 remains in its initial position. In doing so, the system 10 ensures that a defined pattern of LIOB cuts 41 alters the intended target in the lens tissue. Consequently, immediately upon the commencement of the compact LIOB cuts 41, the imaging unit 18 begins to monitor the lens bag 30 for the purpose of detecting any displacement or movement thereof as shown in action block 56. For accomplishing this monitoring step, the imaging unit 18 continuously produces a real-time image of the lens bag 30. This real-time image and the actual image are then used by the computer 16 to detect movement of the lens bag 30 as shown in inquiry block 58. At this point, the computer 16 determines whether the lens bag 30 has moved. If the lens bag 30 has moved, the computer 16 realigns the laser unit 12 as shown in action block 60. Then, once the laser unit 12 is realigned to target the selected segment 40, compact LIOB cuts 41 are again created in the selected segment 40 at action block 54.

In the case where inquiry block 58 determines the lens bag 30 does not move, inquiry block 62 illustrates that a determination is made as to whether additional compact LIOB cuts are required. If additional cuts are required, more cuts are created by the system 10 returning to action block 54. When additional cuts are not required, the selected segment 40 is aspirated at action block 64. Once the selected segment 40 is aspirated, the remaining operational segments 32 are aspirated as indicated by action block 66. During the aspiration of the remaining operational segments 32, the system 10 determines whether additional compact LIOB cuts 41 are required to continue the aspiration at inquiry block 68. If additional compact LIOB cuts are required, the system 10 directs the laser unit 12 to create additional cuts with a return to action block 54. If additional cuts are not required, the system 10 determines whether aspiration of the lens 28 is complete at inquiry block 70. If aspiration is not complete at inquiry block 70, then the lens 28 can be turned using the probe 26 at action block 72. This allows the aspirator 22 to remain stationary and to continue aspirating the lens 28 at action block 74.

When the system 10 indicates that the aspiration of the lens 28 is complete at inquiry block 70 after the lens 28 has been turned, the removal of the lens 28 is complete and the operation of the system 10 ends as indicated by action block 76.

While the particular System and Method for Performing Lens Fragmentation as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A method for preparing the lens of an eye for removal from a lens bag during ophthalmic surgery, the method comprising the steps of:
   sectioning the lens into a plurality of operational segments with Laser Induced Optical Breakdown (LIOB) cuts into the lens; with cuts extending from a center of the lens to an edge of the lens between an anterior surface and a posterior surface of the lens;
   selecting at least one operational segment;
   creating compact LIOB cuts on tissue in the selected segment to soften lens tissue in the selected segment;
   providing a computer for guiding a focal point of a laser beam in a predetermined pattern during the sectioning step, and for guiding the focal point in a defined pattern during the creating step;
   imaging the lens bag of the eye prior to the creating step to establish an initial image of the lens bag;
   producing an actual image of the lens bag in real-time during the creating step;
   using the computer to compare the initial image of the lens bag with the actual image of the lens bag to identify a difference therebetween, wherein the computer using the difference to guide the focal point of the laser beam to compensate for the difference;
   moving the lens in the lens bag with a probe to facilitate an aspiration of tissue from the lens bag; and
   wherein the selected segment is less than one third of the lens, by volume.

2. A method as recited in claim 1 wherein the imaging step is accomplished with a device having an imaging capability selected from a group comprising confocal microscopy, Optical Coherence Tomography (OCT) imaging, second-harmonic imaging, video imaging, still photo imaging and Scheimpflug imaging.

3. A method as recited in claim 1 further comprising the steps of:
   aspirating, in sequence, softened lens tissue in the selected segment, and un-softened tissue in the operational segments outside the selected segment; and
   irrigating the lens bag during the aspirating step.

4. A method as recited in claim 3 wherein the aspirating step, the irrigating step, and the moving step are accomplished robotically with input commands entered into a robotic interface device connected to the computer.

5. A method as recited in claim 4 wherein the aspirating step is accomplished using an aspirator, and the irrigating step is accomplished by an irrigator, wherein the aspirator, the irrigator, and the probe are electronically connected to the computer and are responsive to input commands entered into the robotic interface device.

6. A method as recited in claim 4 wherein the moving step comprises the step of:
   turning the lens inside the lens bag with the probe to reposition the lens therein for aspiration of lens tissue therefrom.

7. A method as recited in claim 1 wherein each operational segment is a quadrant of the lens.

8. A method as recited in claim 1 wherein the lens defines an axis, and the LIOB cuts from the sectioning step are selected from a group comprising radial cuts extending outwardly from the axis and ring cuts centered on the axis.

9. A method as recited in claim 8 further comprising the step of creating at least one disk layer cut into the lens tissue, wherein the disk layer cut is perpendicular to the axis.

10. A method for preparing the lens of an eye for removal from a lens bag during ophthalmic surgery, the method comprising the steps of:
    sectioning the lens into a plurality of operational segments using a predetermined pattern of Laser Induced Optical Breakdown (LIOB) cuts wherein each operational segment is greater than 5% and less than 40% of the lens, by volume and each cut extends from a center of the lens to an edge of the lens between an anterior surface and a posterior surface of the lens;
    creating compact LIOB cuts in a defined pattern on tissue within a selected segment of the lens to soften lens tissue in the selected segment for removal from the lens bag, wherein the selected segment includes at least one operational segment;
    providing a computer for guiding a focal point of a laser beam in a predetermined pattern during the sectioning step, and for guiding the focal point in a defined pattern during the creating step;
    imaging the lens bag of the eye prior to the creating step to establish an initial image of the lens bag;
    producing an actual image of the lens bag in real-time during the creating step;
    using the computer to compare the initial image of the lens bag with the actual image of the lens bag to identify a difference therebetween, wherein the computer uses the difference to guide the focal point of the laser beam to compensate for the difference; and
    moving the lens in the lens bag with a probe to facilitate an aspiration of tissue from the lens bag.

* * * * *